US006479672B1

(12) United States Patent
Houpis et al.

(10) Patent No.: US 6,479,672 B1
(45) Date of Patent: Nov. 12, 2002

(54) DIASTEREOSELECTIVE PREPARATION OF MICHAEL ADDUCTS

(75) Inventors: Ioannis Houpis, Plainfield, NJ (US); Ralph P. Volante, Cranbury, NJ (US); Fengrui Lang, Piscataway, NJ (US); Ilias Dorziotis, Bridgewater, NJ (US); David Tschaen, Holmdel, NJ (US); Shinji Kato, Nagoya, NJ (US); Toshiaki Mase, Okazaki, NJ (US)

(73) Assignees: Merck & Co., Inc., Rahway, NJ (US); Banyu Pharmaceutical Co., Ltd,, Tokyo (JP)

( * ) Notice: Subject to any disclaimer, the term of this patent is extended or adjusted under 35 U.S.C. 154(b) by 0 days.

(21) Appl. No.: 09/545,313

(22) Filed: Apr. 7, 2000

Related U.S. Application Data

(60) Provisional application No. 60/128,258, filed on Sep. 8, 1999, and provisional application No. 60/163,596, filed on Nov. 4, 1999.

(51) Int. Cl.$^7$ .................. C07D 317/34; C07D 295/12
(52) U.S. Cl. ........................................................ 549/267
(58) Field of Search ........................................ 549/267

(56) References Cited

U.S. PATENT DOCUMENTS 5,948,792 A    9/1999   Tsuchiya et al.

OTHER PUBLICATIONS

Deoxofluor Product Brochure. Air Products, Allentown, PA 1998.

*Primary Examiner*—Mukund J. Shah
*Assistant Examiner*—Thomas McKenzie
(74) *Attorney, Agent, or Firm*—Mollie M. Yang; David L. Rose

(57) ABSTRACT

Michael addition conducted in the presence of a zinc-amine complex and additional amounts of the amine component results in product with high diastereomeric excess.

10 Claims, No Drawings

DIASTEREOSELECTIVE PREPARATION OF MICHAEL ADDUCTS

CROSS-REFERENCE TO RELATED APPLICATIONS

This application is a non-provisional application related to U.S. application Ser. No. 60/128,258, filed on Apr. 8, 1999 and Ser. No. 60/163,596, filed on Nov. 4, 1999 priority of which is claimed hereunder.

SUMMARY OF THE INVENTION

The present invention relates to diastereoselective Michael addition using zinc-amine complex reagent. and further provides a method for the diastereoselective preparation of α-hydroxyacetic acids.

BACKGROUND OF THE INVENTION

U.S. Pat. No. 5,948,791 discloses fluorine-containing 1,4-disubstituted piperidine derivatives. These compounds are muscarinic M3 receptor antagonists useful for the treatment or prophylaxis of respiratory diseases such as chronic obstructive pulmonary diseases, chronic bronchitis, asthma and rhinitis; digestive diseases such as irritable bowel syndrome, convulsive colitis, diverticulitis and pain accompanying contraction of smooth muscles of the digestive system; urinary disorders like urinary incontinence and frequency in neurogenic pollakiuria, neurogenic bladder, nocturnal enuresis, unstable bladder, cystospasm and chronic cystisis; and motion sickness.

Many of the derivatives exemplified in U.S. Pat. No. 5,948,792 are of the formula (A)

(A)

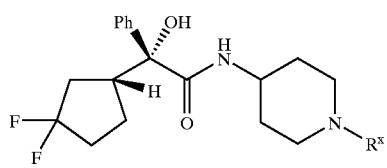

where $R^x$ is defined in the patent as $R^2$. Their synthesis requires the common precursor (2R)-[(1R)-3,3-difluorocyclopentyl]-2-hydroxy-2-phenylacetic acid, which may be prepared according to the methods disclosed in U.S. Pat. No. 5,948,792 and summarized in the following scheme:

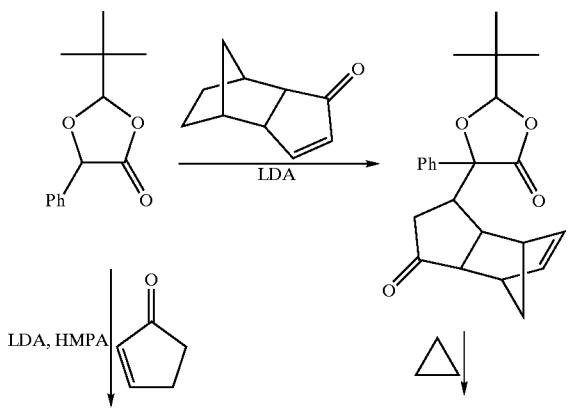

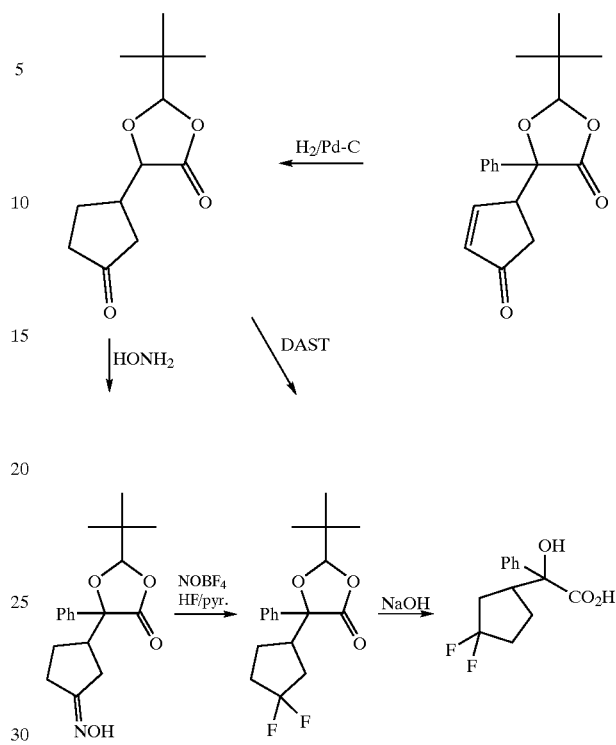

The Michael addition of a dioxolanone to a cyclopentenone is the key step in defining the stereochemistry of the phenylacetic acid precursor. The methods described in U.S. Pat. No. 5,948,792 are not suitable for large-scale preparation of the chiral phenylacetic acid—the use of the chiral tricyclic ketone is prohibitively expensive and involves flash pyrolysis requiring specialized equipment, and deprotonation of cyclopentenone using lithium diisopropylamide (LDA) in hexamethylphosphoramide (HMPA) does not impart diastereocontrol to the Michael addition. There is therefore the need for an efficient and stereoselective process amenable to large-scale production to provide the phenylacetic acid precursor of the desired stereochemistry.

DETAILED DESCRIPTION OF THE INVENTION

The present invention provides a process for the diastereoselective preparation of Michael adducts of a cycloalkenone and a chiral 2,5-disubstituted-1,3-dioxolan-4-one using a zinc-amine complex and the free amine of the zinc-amine complex. The novel process comprises the steps of:

(a) contacting said chiral 2,5-disubstituted-1,3-dioxolan-4-one with a base to provide the corresponding enolate;

(b) contacting said enolate with a zinc-amine complex followed by addition of the free amine component of the zinc-amine complex;

(c) contacting the mixture of step (b) with the cycloalkenone.

The term "diastereoselective" as used herein means that the desired isomer is formed predominantly, i.e. 50% or greater of the diastereomeric mixture.

The chiral 2,5-disubstituted-1,3-dioxolan-4-one is preferably a compound of formula (I):

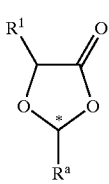

in which $R^1$ is an optionally substituted hydrocarbyl group such as optionally substituted aryl, optionally substituted $C_{1-6}$alkyl, optionally substituted $C_{2-6}$alkenyl or optionally substituted $C_{2-6}$alkynyl, where the substituents may be for example hydroxy, thiol, ethers, thioethers, primary, secondary and tertiary amines; $R^a$ is a bulky group such as t-butyl, phenyl, diphenylmethyl, trityl, trichloromethyl, mesityl, or the like; the asterisk (*) indicates that the chiral center is of defined 3-dimensional configuration.

The base may be any that is capable of generating an enolate of the dioxolanone described above; examples of suitable bases include lithium diisopropylamide (LDA), lithium hexamethyldisilazide, lithium t-butoxide, sodium t-butoxide, DBU and tetramethyguanidine, and the like. Preferably a lithium base is used to generate the lithium enolate.

For the zinc-amine complex, the zinc component may be any zinc (II) compounds such as zinc chloride, zinc bromide, zinc iodide, zinc trifluoromethanesulfonate and the like. The amine component is an amine containing at least two nitrogen atoms separated by 2 to 6 atoms. Preferably the amine is a secondary or tertiary amine, more preferably a tertiary amine; suitable amines are, for example, of the formula (IV):

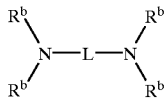

wherein L is $C_{2-6}$ alkylene or $C_{2-6}$ alkenyl each of which may be optionally interrupted by a heteroatom selected from O, S and N—$R^c$ wherein $R^c$ is H or $C_{1-6}$ alkyl; each $R^b$ is independently H or $C_{1-4}$ alkyl or 2 $R^b$s together with the N to which they are attached form a 5- or 6-membered ring optionally containing an additional heteroatom selected from O, S and N—$R^c$ wherein $R^c$ is H or $C_{1-6}$alkyl. Examples of suitable amines are 4-[2-(dimethylamino)ethyl] morpholine; N,N-diethyl-N',N'-dimethylethylenediamine; 1-[2(dimethylamino)ethyl]-4-methylpiperazine; N,N,N',N'-tetramethylethylenediamine; 1-[2(dimethylamino)ethyl] pyrrolidine; 1-[(2-(dimethylamino)ethyl]piperidine; N,N', N'-tetramethyl-1,3-propanediamine; N,N,N',N'-tetramethyl-1,4-butanediamine; 1-[3-(dimethylamino)propyl]-4-methylpiperazine; 1-[3-(dimethylamino)propyl]-4-ethylpiperazine; 1-[3-(dimethylamino)propyl]piperidine; 1-[3-(dimethylamino)propyl]pyrrolidine; 1-[3-(dimethylamino)propyl]morpholine; N,N-bis-[2-(dimethylamino)ethyl]-N-methylamine; bis-[2-(dimethylamino)ethyl]ether. The preferred amine is selected from 4-[2-(dimethylamino)ethyl]morpholine; N,N-diethyl-N',N'-dimethylethylenediamine; 1-[2(dimethylamino) ethyl]-4-methylpiperazine; N,N,N',N'-tetramethylethylenediamine; 1-[2(dimethylamino)ethyl] pyrrolidine; and 1-[(2-(dimethylamino)ethyl]piperidine.

The cycloalkenone of the present process is a compound of formula (II):

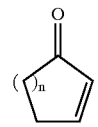

wherein n is 1, 2 or 3.

The novel process, in one embodiment, is illustrated in the following scheme:

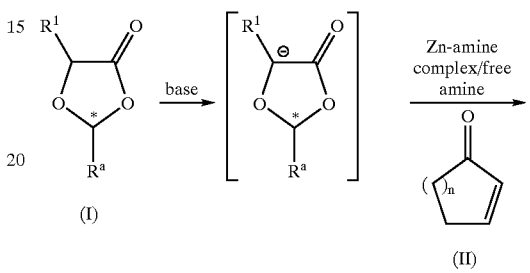

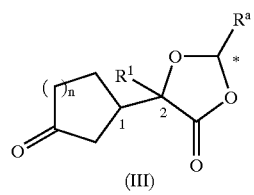

In the novel process, the product Michael adduct (III) is obtained as a mixture of diasteromers with the predominant diastereomer being determined by the configuration at the * carbon. For example, when the configuration at the * carbon is R, the predominant diastereomer of the Michael adduct has the R/R configuration at carbon atoms 1/2, and when the configuration at the * carbon is S, the predominant isomer has the S/S configuration at carbon atoms 1/2.

In the present process, the chiral dioxolanone is first treated with a base to generate the corresponding enolate. In one preferred embodiment the chiral dioxolane is a compound of formula (I) wherein $R^1$ is phenyl and $R^a$ is t-butyl. Preferably the base is lithium base such as lithium diisopropylamide and lithium hexamethyldisilazide. The base is preferably used in excess relative to the dioxolane, for example up to about 1.5 equivalents. The reaction is carried out under inert atmosphere at a temperature of −25° C. or lower and in an aprotic organic solvent such as tetrahydrofuran, dimethoxyethane, toluene or other aromatic solvents, diethyl ether or methyl t-butyl ether, or a mixture thereof.

The resultant enolate is treated with a zinc-amine complex while maintaining the reaction temperature at below about −30° C., for example from −45 to about −30° C. The zinc-amine complex may be used in from about 0.2 to about 2 equivalents relative to the dioxolane. After about an hour, additional free amine is added to the mixture. The free amine is used in about two to about twenty equivalents relative to the dioxolane, preferably about two to about four equivalents. For the zinc-amine complex, the zinc component is preferably zinc chloride, and the amine is preferably selected from 4-[2-(dimethylamino)ethyl]morpholine; N,N-diethyl- N',N'-dimethylethylenediamine; 1-[2(dimethylamino) ethyl]-4-methylpiperazine; N,N,N', N'tetramethylethylenediamine; 1-[2(dimethylamino)ethyl] pyrrolidine; and 1-[(2-dimethylamino)ethyl]piperidine. The reaction mixture is maintained at about −20° to about 0° C. for about 30 minutes to about three hours. The mixture is then cooled to, for example, about −78° C., and the cycloalkenone is added thereto. The cycloalkenone is added gradually such that the temperature of the reaction mixture does not exceed about −65° C. for example between about −65 to −78° C. The reaction is generally complete within about three hours.

In another aspect the present invention provides a diastereoselective process for the preparation of an α-hydroxy acetic acid of the formula (V) or salts thereof

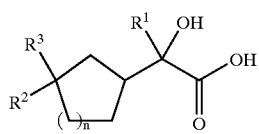
(V)

wherein n is 1, 2 or 3;

$R^1$ is an optionally substituted hydrocarbyl group;

$R^2$ and $R^3$ are independently H, halogen, $C_{1-6}$ alkyl, $C_{2-6}$ alkenyl, $C_{2-6}$ alkynyl, $C_{3-7}$ cycloalkyl, $OR^d$, $NR^dR^e$; wherein $R^d$ and $R^e$ are independently H, $C_{1-6}$ alkyl, aryl, $C_{3-7}$ cycloalkyl, $C(O)R^d$, or $R^d$, $R^e$ together with the N to which they are attached form a 5- or 6-membered ring optionally containing a heteroatom selected from O, S or $NR^c$; $R^c$ is H or $C_{1-6}$alkyl; or $R^2+R^3$ is oxo which comprises (a) contacting a chiral 2,5-disubstituted-1,3-dioxolan-4-one of formula (I)

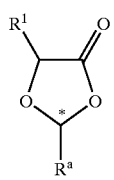
(I)

with a lithium base to provide the corresponding lithium enolate;

(b) contacting said enolate with a zinc-amine complex followed by addition of the free amine;

(c) contacting the mixture of step (b) with a 5- or 6-membered cycloalkenone of formula (II)

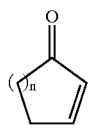
(II)

to form a Michael adduct of formula III

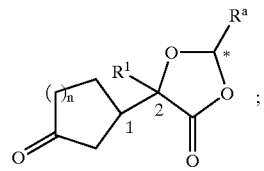
(III)

(d) optionally converting the keto group on the cycloalkane group of the Michael adduct (III) to $R^2$ and $R^3$ wherein $R^2$ and $R^3$ are other than oxo; and (e) treating the product of step (c) or (d) with a base to provide the compound of formula (V).

Steps (a), (b) and (c) are discussed in detail hereinabove. In Step (d) the keto group on the cycloalkane group of the Michael adduct (III) may be transformed into other substituents such as hydroxy, amino, halogen, alkyl, alkenyl, and the like, or it may be removed to provide the unsubstituted cycloalkane. These chemical manipulations may be performed using well known chemical reactions such as hydrogenation, hydride reduction, Grinard reaction, Wittig reaction, reductive amination, halogenation; these and other suitable reactions are described in standard textbooks such as March, Advanced Organic Chemistry (3rd Edition, Wiley-Interscience).

More particularly, the keto group may be converted to gem-difluoro using fluorinating reagents such as DAST or $NOBF_4$. In a more preferred method, difluorination is accomplished using bis(2-methoxyethyl)aminosulfur trifluoride (Deoxo-Fluor™, Air Products, Allentown, Pa.). The difluorination using bis(2-methoxyethyl)aminosulfur trifluoride is carried out in an aprotic, nonpolar organic solvent, preferably non-ethereal solvent, or a mixture thereof, and preferably in the presence of a proton source such as water, alcohol, an organic or inorganic acid such as trifluoroacetic acid, or in the presence of a Lewis acid such as boron trifluoride etherate or gallium trichloride. The proton source or Lewis acid is present in about 5 to about 20 mole percent of the starting ketone. It has been found that the combination of trifluoroacetic acid or boron trifluoride etherate and toluene is particularly advantageous. The reaction is carried out at elevated temperature, e.g., from about 30 to about 60° C. and the reaction is generally complete within 24 hours.

The Michael adduct or a keto-modified derivative thereof may be converted to the corresponding α-hydroxyacetic acid (V) using base-induced hydrolysis. A base such as lithium hydroxide, sodium hydroxide, potassium hydroxide, potassium carbonate and the like may be used, and the reaction is carried out at elevated temperature of about 30 to about 60° C. The acid (V) may be converted to an organic or inorganic base salt such as the dicyclohexylamine, benzylamine, diethylamine, lithium, sodium and potassium salts using conventional chemical techniques.

The α-hydroxyacetic acid (V) may be used to couple with an amine of the formula (B) or salts thereof:

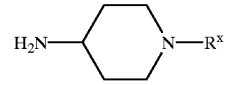
(B)

($R^x$ is as defined in U.S. Pat. No. 5,948,792 as $R^2$) to provide compounds of formula (A). The coupling of the acid of formula (V) and the amine of formula (B) may be carried out under conventional amide formation conditions. Thus, the reaction may be carried out in the presence of coupling agents such as a carbodiimide (e.g., 1-ethyl-3-(3-dimethylaminopropyl)carbodiimide) and hydroxybenzotriazole. The acid may also be converted into an acylating equivalent, such as the corresponding acid chloride, and reacted with the amine compound in the presence of a base such as secondary and tertiary amines.

The following examples are provided to illustrate the invention and are not to be construed as limiting the scope of the invention in any manner.

EXAMPLE 1

(2R,5R)-2-(tert-Butyl)-5-[(1R)-3-oxocyclopentyl]-5-phenyl-1,3-dioxolan-4-one Using 1-[2-(Dimethylamino)ethyl]-4-methylpiperazine Dimethoxyethane (440 mL), in a 5 L 3-neck round bottom flask under $N_2$, was cooled to −40° C. followed by addition of lithium diisopropylamide (1.77 M in heptane-ethylbenzene-THF; 360 mL, 636 mmol, 1.4 eq.). A solution of (2R,5R)-2-(tert-butyl)-5-phenyl-1,3-dioxolan-4-one (100 g, 454 mmole) in dimethoxyethane (880 mL, required heating to 35° C. for complete dissolution) was added maintaining the internal temperature ≦−35° C. The resulting solution was aged for 15 min. at ca −35° C. and then the zinc (II) chloride·1-[2-(dimethylamino)ethyl]-4-methylpiperazine complex (Example 12, 181.58 g, 590 mmole; 1.3eq.) was added as a solid under a $N_2$ blanket. The resulting slurry was aged for 1 h at −35 to −30° C. and then 1-[2-(dimethylamino)ethyl]-4-methylpiperazine (351 mL, 1.816 mole, 4 eq.) was added followed by toluene (1.32 L). The mixture was aged for 3 h at −30 to −35° C. and then cooled to −78° C. A solution of 2-cyclopenten-1-one (41.8 mL; 499 mmole; 1.1 eq.) in toluene (132 mL) was added over 1 h so that the temperature did not exceed −73° C. and the reaction mixture was aged at −78° C. for 45 minutes. Once HPLC analysis indicated that the reaction was complete, $H_2SO_4$ (4M; 100 mL) was added to the mixture, raising the temperature to ca −50° C. The mixture was transferred into a cooled $H_2SO_4$ solution (4M; 900 mL) at such a rate that the temperature did not exceed 10° C. The reaction vessel was washed with 400 mL of $H_2SO_4$ (4M) and 400 mL of ethyl acetate and the washings were combined with the mixture in the quench vessel. Solid NaCl (70 g) was added and the mixture stirred for 20 minutes. The layers were separated, the organic layer was washed sequentially with sat. $NaHCO_3$ (400 mL) and brine (300 mL) and then dried over $Na_2SO_4$. The solution was filtered and assayed to give a ratio of RRR:SRR:SSR=86.4:4.7:8.9. Assay yield of desired compound 111 g, 81%.

The worked-up solution above was solvent switched to ethanol by repeated concentrations and additions of ethanol, and the volume of the solution was adjusted to ca 5 mL/g (550 mL). The solvent amount was checked by NMR (ethanol:Michael adduct molar ratio=20:1.)

The mixture was heated to 50° C. for complete dissolution, then cooled to 40° C. and seeded. The resulting slurry was allowed to cool to 18° C. and charged with 20 mL/g ethanol:methanol:$H_2O$ (1:1:2) (550 mL:550 mL:1100 mL) over 2 hours.

The slurry was then aced at ambient temperature for 18 hours and then cooled to 0° C. for 6 hours [LC Area% RRR:SRR:SSR=6.9%:5%:8.9% in the mother liquors].

The slurry was then filtered at 0° C., the filter cake washed with 3 mL/g of cold (0° C.) ethanol:methanol:$H_2O$ (2:1:2) (330 mL×2) and dried in vacuo under $N_2$ sweep.

EXAMPLE 2

(2R,5R)-2-(tert-Butyl)-5-[(1R)-3-oxocyclopentyl]-5-phenyl-1,3-dioxolan-4-one Using 1-[2-(dimethylamino)ethyl]-4-methylpiperazine To dry 1,2-dimethoxyethane (440 mL) were added dropwise a solution of lithium diisopropylamide in tetrahydrofuran (1.90 M, 335 mL, 636 mmol) below −30° C. under nitrogen atmosphere, and then a solution of (2R,5R)-2-(tert-butyl)-5-phenyl-1,3-dioxolan-4-one (100 g, 454 mmol) in dry 1,2-dimethoxyethane (880 mL) below −30° C. The mixture was stirred at −30° C. for 15 minutes. To the mixture was added in one portion a solid of zinc (II) chloride·1-[2-(dimethylamino)ethyl]-4-methylpiperazine complex (182 g, 590 mmol) below −30° C. under nitrogen flow. After stirring at −30° C. for 1 hour, dry 1-[2-(dimethylamino)ethyl]-4-methylpiperazine (351 mL, 1.82 mol) and dry toluene (1,320 mL) were added to the slurry below −30° C. The resulting mixture was warmed to 0° C. and aged at 0–5° C. for 1 hour, and then cooled to −78° C. To the resulting slurry was added dropwise a solution of 2-cyclopenten-1-one (41.8 mL, 499 mmol) in dry toluene (132 mL) below −77° C. over a period of 30 minutes, and the mixture was stirred at −78° C. for 50 minutes. After the addition of 4M sulfuric acid (100 mL), the heterogeneous mixture was transferred into a cold 4M sulfuric acid (1,200 mL) with ice-cooling below 10° C. Ethyl acetate (900 mL) and sodium chloride (65 g) were added, and the mixture was stirred at 10–15° C. for 15 minutes, and then separated. The organic layer was washed with saturated aqueous sodium bicarbonate (400 mL) and brine (300 mL), dried over anhydrous sodium sulfate, and then concentrated under reduced pressure to 1,200 mL. The solution was assayed by HPLC: RRR:114.6 g assay, 84% yield, RRR:SRR:SSR=90.6:1.6:7.8

HPLC Condition

Column: ZOBAX RX-C8; Column size: ID 4.6 mm, Length 250 mm, Particle size 5 μm; Column temperature: 45° C.; Flow rate: 1.5 mL/min.; Indicator: 210 nm; Injection volume: 5 μl;

Eluent: methanol-$H_2O$—$H_3PO_4$(60:40:0.1)

HPLC Condition for Ratio Determination

Column: ZOBAX RX-C8; Column size: ID 4.6 mm. Length 250 nm, Particle size 5 μm; Column temperature: 30° C.; Flow rate: 1.0 mL/min.; Indicator: 210 nm; Injection volume: 10 μl;

| Eluent: | min. | methanol | $H_2O$ |
| --- | --- | --- | --- |
| | 0 | 55 | 45 |
| | 10 | 40 | 60 |
| | 40 | 30 | 70 |

The above solution was further concentrated to 458 mL. The solvent was changed from ethyl acetate to ethanol by addition of ethanol and then concentration. The resulting ethanol solution (573 mL) was heated to 50° C. and then allowed to cool. At 38–40° C. the solution was seeded. The slurry was aced at 21° C. for 1 hour, and then ethanol-methanol-water mixture (1:1:2, 2,290 mL) was added dropwise over a period of 2 hours. The slurry was aged at 17–21° C. for 13 hours and then at 0–5° C. for 6 hours, and filtered under nitrogen flow. The cake was washed 3 times with cold ethanol-methanol-water mixture (2:1:2, 344 mL) and dried under nitrogen flow then at 30° C. under reduced pressure overnight. The title compound (101 g, 74% yield, RRR:SRR:SSR=99.69:0.16:0.15 by HPLC analysis) was obtained as pale yellow crystals.

MP 117° C. UV (λ max, nm) 257. IR (KBr, cm$^{-1}$): 3,450:2,970; 1,800; 1,740; 1220: 1,120. $^1$-NMR (CDCl$_3$, δ ppm): 0.93 (9H, s), 1.8–2.0 (2H, m), 2.1–2.3 (3H, m), 2.34 (1H, m), 2.90 (1H, m), 5.44 (1H, s), 7.2–7.5 (3H, m), 7.67 (2H, d, J=6.9 Hz)

EXAMPLE 3

(2R,5R)-2-(tert-Butyl)-5-[(1R)-3-oxocyclopentyl]-5-phenyl-1,3-dioxolan-4-one Using 4-[2-(dimethylamino)ethyl]morpholine To dry 1,2-dimethoxyethane (13 mL) were added dropwise a solution of lithium diisopropylamide in tetrahydrofuran (1.79 M, 10 mL, 17.9 mmol) below −30° C. under nitrogen atmosphere, and then a solution of (2R,5R)-2-(tert-butyl)-5-phenyl-1,3-dioxolan-4-one (3 g, 13.62 mmol) in dry 1,2-dimethoxyethane (27 mL) below −30° C. The mixture was stirred at −30° C. for 15 minutes. To the mixture were added in one portion a solid of zinc (II) chloride·4-[2-(dimethylamino)ethyl]morpholine complex (5.22 g, 17.72 mmol) and dry 1,2-dimethoxyethane (1 mL) below −30° C. under nitrogen flow. After stirring at −30° C. for 1 hour, dry 4-[2-(dimethylamino)ethyl]morpholine (9.4 mL, 54.94 mmol) and dry toluene (41 mL) were added to the slurry below −30° C. The resulting mixture was warmed to −25° C. and aged at −25° C. for 3 hours. and then cooled to −78° C. To the resulting slurry was added dropwise a solution of 2-cyclopenten-1-one (1.25 mL, 14.92 mmol) in dry toluene (5 mL) below −77° C. over a period of 30 minutes, and the mixture was stirred at −78° C. for 45 minutes. After the addition of 4M sulfuric acid (3 mL), the heterogeneous mixture was transferred into a cold 4M sulfuric acid (33 mL) with ice-cooling below 10° C. Ethyl acetate (55 mL) was added, and the mixture was stirred at 10–15° C. for 15 minutes, and then separated. The organic layer was washed with water (30 mL), saturated aqueous sodium bicarbonate (30 mL) and brine (15 mL), dried over anhydrous magnesium sulfate, and then concentrated under reduced pressure to 80 mL. The solution was assayed by HPLC: RRR 3.02 g assay, 73% yield; RRR:SRR:SSR=88.6:2.3:9.1

EXAMPLE 4

(2R,5R)-2-(tert-Butyl)-5-[(1R)-3-oxocyclopentyl]-5-phenyl-1,3-dioxolan-4-one Using N,N-Diethyl-N',N'-dimethylethylenediamine To dry 1,2-dimethoxyethane (9 mL) were added dropwise a solution of lithium diisopropylamide in tetrahydrofuran (1.79 M, 6.6 mL, 11.81 mmol) below −30° C. under nitrogen atmosphere, and then a solution of (2R,5R)-2-(tert-butyl)-5-phenyl-1,3-dioxolan-4-one (2 g, 9.08 mmol) in dry 1,2-dimethoxyethane (18 mL) below −30° C. The mixture was stirred at −30° C. for 15 minutes. To the mixture were added in one portion a solid of zinc (II) chloride·N,N-diethyl-N',N'-dimethylethylenediamine complex (3.31 g, 11.80 mmol) and dry 1,2-dimethoxyethane (1 mL) below −30° C. under nitrogen flow. After stirring at −30° C. for 1 hour, dry N,N-diethyl-N',N'-dimethylethylenediamine (5.24 g, 36.32 mmol) and dry toluene (28 mL) were added to the slurry below −30° C. The resulting mixture was warmed to −25° C. and aged at −25° C. for 3 hours, and then cooled to −78° C. To the resulting slurry was added dropwise a solution of 2-cyclopenten-1-one (0.84 mL, 10.03 mmol) in dry toluene (5 mL) below −77° C. over a period of 30 minutes, and the mixture was stirred at −78° C. for 45 minutes. After the addition of 4M sulfuric acid (2 mL), the heterogeneous mixture was transferred into a cold 4M sulfuric acid (25 mL) with ice-cooling below 10° C. Ethyl acetate (40 mL) was added, and the mixture was stirred at 10–15° C. for 15 minutes, and then separated. The organic layer was washed with water (20 mL), saturated aqueous sodium bicarbonate (20 mL) and brine (10 mL), dried over anhydrous magnesium sulfate, and then concentrated under reduced pressure to 50 mL. The solution was assayed by HPLC: RRR 1.97 g assay, 72% yield; RRR:SRR:SSR=86.6:5.0:8.4

EXAMPLE 5–8

The general procedure described in Example 2 was followed using the following amines and its zinc (II) chloride complexes instead of 4-[2-(dimethylamino)ethyl]morpholine and zinc (II) chloride·4-[2-(dimethylamino)ethyl]morpholine complex.

N,N,N',N'-tetramethylethylenediamine
RRR isomer yield(assayed by HPLC): 72% (3.98 g); Stereoisomer composition(assayed by HPLC): RRR:SRR:SSR=81.8:7.6:10.6.

1-[2-(dimethylamino)ethyl]pyrrolidine (see Remenar, Julius F. et al., J. Ame. Chem. Soc., 119(24) 5567–5572(1997) and Granger, R. et al., Chim. Ther., 3 (2) 129–135(1968))
RRR isomer yield(assayed by HPLC): 72% (1.98 g); Stereoisomer composition(assayed by HPLC): RRR:SRR:SSR=86.2:3.5:10.3.

1-[2-(dimethylamino)ethyl]piperidine (see Watanabe Y. et al., Bull. Chem. Soc. Jpn. 49(8) 2302–2305(1976) and Dell, Hans D. et al., Arch. Pharm. Ber. Dtsch. Pharm. Ges., 300(11) 933–939(1967))
RRR isomer yield(assayed by HPLC): 72% (2.97 g); Stereoisomer composition(assayed by HPLC): RRR:SRR:SSR=87.3:2.7:10.0.

N,N,N',N'-tetramethyl-1,3-propanediamine
RRR isomer yield (assayed by HPLC): 72% (2.95 g); Stereoisomer composition(assayed by HPLC): RRR:SRR:SSR=84.5:7.5:8.1.

EXAMPLE 9

(2R,5R)-2-(tert-Butyl)-5-[(1R)-3,3-difluorocyclopentyl]-5-phenyl-1,3-dioxolan-4-one Method A. bis(2-methoxyethyl)aminosulfur trifluoride (1.65 L, 8.98 mole, 2.7 eq.) and trifluoroacetic acid (50 mL, 0.65 mole, 0.2 eq.) in toluene (0.5 L) were added to toluene (2 L) in a 5 gal. hasteloy reactor cooled to 5° C. A solution of (2R,5R)-2-(tert-butyl)-5-[(1R)-3-oxocyclopentyl]-5-phenyl-1,3-dioxalin-4-one (1.0 kg, 3.31moles) in toluene (2 L) was charged in one portion and the mixture was heated to 40° C. for 22 hours. The batch was cooled to 35° C. and transferred to a polyjug while the reactor was washed with methyl t-butyl ether (2 L).

A 100 L extractor was charged with methyl t-butyl ether (18 L), the reactor wash (2 L), and 1 N NaOH (25 L). The mixture was precooled to 0° C., and the batch was slowly added via pump so that the internal temperature did not exceed 18° C. After the quench was complete the pH of the aqueous layer was checked and adjusted to ca 12 with 5 N NaOH. The layers were separated and the organic layer was washed with 2N HCl (10 L) and water (10 L). The organic layer was concentrated in vacuo on the rotovap, and dissolved in methanol (10 L).

Method B. bis(2-methoxyethyl)aminosulfur trifluoride (10.5 kg) was dissolved in toluene (28 L) in a Teflon or Hasterlloy reactor and chilled to 5° C. Borontrifluoride etherate (450 mL) was dissolved in 2 L of toluene and added to the bis(2-methoxyethyl)aminosulfur trifluoride solution. The mixture was aged for 2 hr at 5° C. (2R,5R)-2-(tert-butyl)-5-[(1R)-3-oxocyclopentyl]-5-phenyl-1,3-dioxolan-4-one (10 kg) was dissolved in toluene (30 L) and the resulting solution was added to the previous mixture after the 2 hr age. The resulting solution was heated at 55° C. for 30 to 40 hr. The aged mixture was cooled to room temperature and added to a pre-cooled (5° C.) mixture of NaOH (2 N, 200 L) and toluene (200 L), maintaining the internal temperature <18° C. After aging for 30 min the aqueous layer was removed and the organic layer was washed with NaOH (2 N, 100 L). The organic layer from the above reaction was washed with deionized water (100 L), then evaporated and solvent switched to a methanol solution of a volume of 110 L (100 L methanol).

EXAMPLE 10

(2R)-[(1R)-3,3-Difluorocyclopentyl]-2-hydroxy-2-phenylacetic Acid Dicyclohexylamine Salt The methanol solution of (2R,5R)-2-(tert-butyl)-5-[(1R)-3,3-difluorocyclopentyl]-5-phenyl-1,3-dioxolan-4-one from Example 9 was treated with LiOH (2N, 7.5 L, 15 moles, 4.5 eq.) and the mixture was heated to 40° C. for 20 hours. Upon completion of the reaction, the mixture was cooled to 30° C., transferred to a 100 L extractor and washed with hexane (20 L). The layers were separated and the aqueous layer cooled to 7° C. and treated with isopropyl acetate (25 L) and 3 N HCl to pH2.5 to 3.

The layers were separated, the organic layer washed with water and then the layers were separated again. The organic layer was treated with Darco G-60 activated carbon (500 g) and the mixture was stirred for 45 minutes at ambient temperature. The slurry was filtered through solka floc and the carbon cake was washed with isopropyl acetate (8 L).

The organic solution was solvent-switched to methyl-ethyl ketone (24 L), warmed to 60° C. and dicyclohexylamine (606 mL, 3.04 mole, 1 eq.) was added in one portion. The resulting solution was aged for 1.5 h at 55–60° C. Crystallization initiated spontaneously, and the slurry was cooled slowly to ambient temperature where it was aged for 4 h. The product was filtered and the filter cake was washed with methyl-ethyl ketone (5 L). The cake was dried in vacuo with a $N_2$ sweep to afford 1.08 kg of an off white solid. Further purification, if needed, can be achieved by dissolving the solid in methanol (12 L) at 55° C. and cooling the solution to 40° C. to induce crystallization. The slurry of the salt in methanol was cooled further to 30° C. and water (18 L) was added over 1 h. The slurry was then cooled to 20° C. and aged for 1.5 h.

The product was filtered and the filter cake was washed with 1:2 methanol:$H_2O$ (1.5 L). The solid was dried under vacuum with $N_2$ sweep at 25° C. to afford 928 g of the salt.

EXAMPLE 11

(2R)-N-[1-(6-Aminopyridin-2-ylmethyl)piperidin-4-yl]-2-[(1R)-3,3-difluorocyclopentyl]-2-hydroxy-2-phenylacetamide In a separation vessel, (2R)-2-[(1R)-3,3-difluorocyclopentyl]-2-hydroxy-2-phenylacetic acid dicyclohexylamine salt (Example 10, 10.0 g, 22.8 mmol; 1 eq.) was mixed with 1.02 N NaOH (65 mL, 2.91 eq, Aldrich), n-heptane (50 mL). The two layers were separated. The bottom aqueous layer was re-extracted with n-heptane (50 mL) and the aqueous layer was mixed with acetonitrile (65 mL), hydroxybenzotriazole hydrate (3.06 g, 22.8 mmol, 1 eq), 2-amino-6-[(4-aminopiperidin-1-yl)methyl]pyridine trihydrochloride (7.56 g, 23.9 mmol, 1.05 eq).

After all of the solid was dissolved, 1-ethyl-3-(3-dimethylaminopropyl)carbodiimide (5.24 g, 27.36 mmol, 1.2 eq) was added. The resulting solution was homogenous. The pH of the solution was about 6. The batch was aged at 35° C. for 4 hrs. then cooled to ≦15° C. and charged with 14 mL 5 N NaOH (3 eq), 65 mL methyl t-butyl ether, and the two layers cut. The quench was exothermic, cold water bath was used to keep the batch ≦30° C.

The organic layer was washed with 2×40 mL 1 N NaOH and separated. To the organic layer was added 34 mL 2N HCl (3 eq) and the lasers cut. To the organic layer was added 30 mL heptane and 11 mL 2N HCl (1 eq) and layers cut again. The top organic layer was discarded and the aqueous layers were combined. The combined aqueous layers were mixed with 65 mL methyl t-butyl ether, cooled to ≦15° C., and then 20 mL 5 N NaOH. The pH of the aqueous layer should be ≧11 (adjust with 5 N NaOH if necessary). Cold water bath was used to cool the batch to room temperature. The two layers were cut and the top organic layer washed with 40 mL brine.

The organic layer was concentrated on a rotavap to about 40 g, flushed with 2×100 mL isopropyl acetate until KF≦400 mcg/ml when the batch is at about 140 g (~150 mL). At this point, some solid may be precipitated. To this was then added more isopropyl acetate (KF≦150 mcg/ml) until total volume is 260 mL (230 g). To the resultant hazy solution was then added 0.5 g Darco G-60 charcoal and the mixture stirred for 1 hr. The mixture was then filtered through a pad of celite (half inch thick) to get a clear solution. The celite cake was washed with 10 ml isopropyl acetate. The filtrate was then concentrated in vacuum to about 90 ml (80 ml isopropyl acetate +9 g product) or 80 g.

The resulting slurry was heated to 70° C. to dissolve all of the solid, then n-heptane was added while keeping the temperature of the batch at 70° C. After 20 ml n-heptane was added, the batch was seeded and aged for 30 min so some crystals were formed. The rest of the n-heptane (total of 160 ml, 2× of the isopropyl acetate volume) was added over 2 hours. The batch was aged at 70° C. for 1 hour and then allowed to cool to room temperature (22° C.) over 1.5 hrs and aged overnight at ambient temperature. The solid product was collected by filtration and cake washed with 2×25 ml 2/1 n-heptane/isopropyl acetate and then 25 ml n-heptane. The product was dried in a vacuum oven under nitrogen sweep at 45° C. overnight to wt 8.0–8.2 g.

EXAMPLE 12

Preparation of Zinc(II)Chloride·1-[2-(Dimethylamino)ethyl]-4-methylpiperazine Complex To a solution of zinc (II) chloride in tetrahydrofuran (0.5M, 300 mL, 150 mmol) was added dropwise 1-[2-(dimethylamino)ethyl]-4-methylpiperazine (38.54 g, 225 mmol) below 20° C. under nitrogen atmosphere. The slurry was stirred at room temperature for 4 hrs., and filtered under nitrogen flow. The cake was washed with dry tetrahydrofuran(100 mL), and dried at room temperature under reduced pressure overnight. The title compound (47.56 g, quantitative yield) was obtained as colorless crystals. mp: ca. 260° C.(dec.). IR(KBr, $cm^{-1}$): 3,430; 2,960; 2,870; 2,820; 1,490; 1,330; 1,190; 1,140; 1,040; 990; 860

REFERENCE EXAMPLE 1

Preparation of (2R,5R)-2-(tert-Butyl)-5-phenyl-1,3-dioxolan-4-one

To a solution of (R)-(−)-mandelic acid (7.00 kg, 46.01 mol) in toluene (70 L) was added dropwise triisopropyl orthoformate (10.51 kg, 55.21 mol) at 24° C., KF=84.3 ppm. The batch was stirred at 24° C. for 2 h. The reaction was monitored by NMR (intermediate:mandelic acid ratio= 82:18). Toluene (70 L) was added to give 170 L total volume and the batch was distilled maintaining a constant volume of 170 L by gradual addition of toluene (70 L). The NMR showed that the starting material was consumed at this time. The batch was concentrated to 70 L at 16° C. After p-toluenesulfonic acid (3 mol %, 262.5 g) was added at 23° C., a solution of pivaldehyde (5.15 kg, 59.81 mol) in toluene (35 L) at 25–28° C. was added over a period of 50 min and the whole was stirred at 28 C. for 30 min. The reaction was monitored by HPLC showing that the reaction was not completed. Additional p-TsOH (3 mol %, 262.5 g) was added at 29° C. and the batch was stirred at 28–26° C. for 15 h. After confirming the completion of the reaction (by HPLC) the batch was diluted with toluene (90 L) to 200 L volume.

HPLC: Mobile phase—methanol:$H_2O$(0.1%v/v $H_3PO_4$)= 60:40; Column—Zorbax Rx-C8; UV—210 nm; Flow rate— 1.5 ml/min; Temperature—45° C.

The batch was washed with 5% aqueous sodium bicarbonate solution (70 L) and 30% aqueous NaCl solution. The organic layer (190 L) contained 10.03 kg 98.9 area %. The same procedure as above was repeated to give 320 L of the organic layer in 98.3 area %, 15.50 kg.

Two batches were combined and then concentrated. To the residue was added 100 L of n-Heptane and the batch was concentrated to 50 L volume. The same procedure was repeated three times to switch the solvent to n-heptane. The resulting slurry was filtered. washed with n-Heptane (2×50 L), and dried under reduced pressure to give the desired compound 23.79 kg in 93.2% yield (98.8% purity).

What is claimed is:

1. A diastereoselective method for preparing a Michael adduct of formula (III)

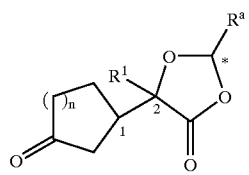

(III)

wherein n is 1, 2 or 3;

$R^1$ is an optionally substituted hydrocarbyl group; and $R^a$ is a bulky group selected from t-butyl, phenyl, diphenylmethyl, trityl, trichloromethyl and mesityl; which comprises (a) contacting a chiral 2,5-disubstituted- 1,3-dioxolan-4-one of formula (I)

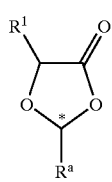

(I)

with a base capable of generating an enolate of said dioxolanone to provide the corresponding enolate;

(b) contacting said enolate with a zinc-amine complex followed by addition of the free amine, wherein the amine of the zinc-amine complex and the free amine are the same and are of formula (IV)

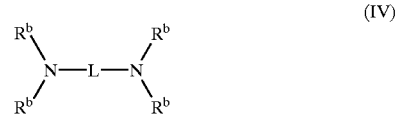

(IV)

wherein

L is $C_{2-6}$ alkylene or $C_{2-6}$ alkenyl each of which may be optionally interrupted by a heteroatom selected from O, S and N—$R^c$ wherein $R^c$ is H or $C_{1-6}$ alkyl;

$R^b$ is independently H or $C_{1-4}$ alkyl; or

2 $R^b$s together with the N to which they are attached form a 5- or 6-membered ring optionally containing an additional heteroatom selected from O, S and N—$R^c$ wherein $R^c$ is H or $C_{1-6}$alkyl; and (c) contacting the mixture of step (b) with a cycloalkenone of formula (II)

(II)

to provide the Michael adduct of formula (III).

2. A process of claim 1 wherein said base is a lithium base.

3. A process of claim 1 wherein said base is selected from lithium diisopropylamide and lithium hexamethyldisilazide.

4. A process of claim 1 wherein said amine is selected from 1-[2-(dimethylamino)ethyl]-4-methylpiperazine, 4-[2-(dimethylamino)ethyl]morpholine, N,N-diethyl-N',N'-dimethylethylenediamine, N,N,N',N'-tetramethylethylenediamine, 1-[2(dimethylamino)ethyl]pyrrolidine, 1-[2-(dimethylamino)ethyl]piperidine, and N,N,N',N'-tetramethyl-1,3-propanediamine.

5. A process of claim 4 wherein said amine is 1-[2-(dimethylamino)ethyl]-4-methylpiperazine.

6. A process of claim 1 wherein said zinc of the zinc amine complex is zinc chloride.

7. A process of claim 1 wherein said zinc-amine complex is zinc (II) chloride·1-[2-(dimethylamino)ethyl]-4-methylpiperazine complex.

8. A process of claim 1 wherein $R^1$ is phenyl and $R^a$ is t-butyl.

9. A process of claim 1 for the preparation of (2R,5R)-2-(tert-butyl)-5-[(1R)-3-oxocyclopentyl]-5-phenyl-1,3-dioxolan-4-one which comprises the steps of:

(a) contacting (2R,5R)-2-(tert-butyl)-5-phenyl-1,3-dioxolan-4-one with a lithium base to generate the lithium enolate;

(b) contacting said enolate with zinc (II) chloride·1-[2-(dimethylamino)ethyl]-4-methylpiperazine complex followed by addition of 1-[2-(dimethylamino)ethyl]-4-methylpiperazine; and (c) contacting the mixture of step (b) with 2-cyclopenten-1-one to provide the Michael adduct.

10. A diastereoselective method for preparing a compound of formula V or salts thereof

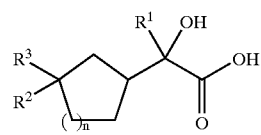
(V)

wherein n is 1 or 2;

$R^1$ is an optionally substituted hydrocarbyl group;

$R^2$ and $R^3$ are independently H, halogen, $C_{1-6}$ alkyl, $C_{1-6}$ alkenyl, $C_{2-6}$ alkynyl, $C_{3-7}$ cycloalkyl, $OR^d$, $NR^dR^e$; wherein $R^d$ and $R^e$ are independently H, $C_{1-6}$ alkyl, aryl, $C_{3-7}$ cycloalkyl, $C(O)R^d$, or $R^d$, $R^e$ together with the N to which they are attached form a 5- or 6-membered ring optionally containing a heteroatom selected from O, S or $NR^c$; $R^c$ is H or $C_{1-6}$ alkyl; or $R^2+R^3$ is oxo which comprises
(a) contacting a chiral 2,5-disubstituted-1,3-dioxolan-4-one of formula (I)

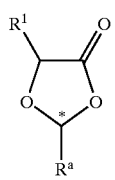
(I)

wherein $R^a$ is a bulky group selected from t-butyl, phenyl, diphenylmethyl, trityl, trichloromethyl and mesityl, with a lithium base capable of generating an enolate of said dioxolanone to provide the corresponding lithium enolate;
(b) contacting said enolate with a zinc-amine complex followed by addition of the free amine, wherein the amine of the zinc-amine complex and the free amine are the same and are of formula (IV)

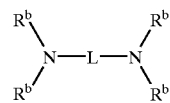
(IV)

wherein

L is $C_{2-6}$ alkylene or $C_{2-6}$ alkenyl each of which may be optionally interrupted by a heteroatom selected from O, S and N—$R^c$ wherein $R^c$ is H or $C_{1-6}$ alkyl;

$R^b$ is independently H or $C_{1-4}$ alkyl; or

2 $R^b$s together with the N to which they are attached form a 5- or 6-membered ring optionally containing an additional heteroatom selected from O, S and N—$R^c$ wherein $R^c$ is H or $C_{1-6}$alkyl;

(c) contacting the mixture of step (b) with a 5- or 6-membered cycloalkenone of formula (II)

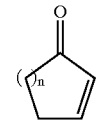
(II)

to form a Michael adduct of formula III

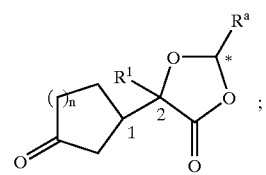
(III)

(d) optionally converting the keto group on the cycloalkane group of the Michael adduct (III) to $R^2$ and $R^3$ wherein $R^2$ and $R^3$ are other than oxo; and
(e) treating the product of step (c) or (d) with a base to provide the compound of formula (V).

* * * * *

UNITED STATES PATENT AND TRADEMARK OFFICE
CERTIFICATE OF CORRECTION

PATENT NO.    : 6,479,672 B1
DATED         : November 12, 2002
INVENTOR(S)   : Ioannis Houpis et al.

It is certified that error appears in the above-identified patent and that said Letters Patent is hereby corrected as shown below:

Column 15,
Line 14, should read -- $R^2$ and $R^3$ are independently H, halogen, $C_{1-6}$ alkyl, $C_{2-6}$ --.

Signed and Sealed this

Twenty-fifth Day of March, 2003

JAMES E. ROGAN
*Director of the United States Patent and Trademark Office*